(12) United States Patent
Nguyen

(10) Patent No.: US 7,666,637 B2
(45) Date of Patent: Feb. 23, 2010

(54) INTEGRATED PROCESS FOR SEPARATION OF LIGNOCELLULOSIC COMPONENTS TO FERMENTABLE SUGARS FOR PRODUCTION OF ETHANOL AND CHEMICALS

(76) Inventor: Xuan Nghinh Nguyen, 3110 E. Cervantes St., #B, Pensacola, FL (US) 32503

( * ) Notice: Subject to any disclaimer, the term of this patent is extended or adjusted under 35 U.S.C. 154(b) by 0 days.

(21) Appl. No.: 11/700,718

(22) Filed: Feb. 1, 2007

(65) Prior Publication Data

US 2008/0057555 A1    Mar. 6, 2008

Related U.S. Application Data

(60) Provisional application No. 60/842,225, filed on Sep. 5, 2006.

(51) Int. Cl.
   *C12P 7/00*    (2006.01)
   *C12P 1/00*    (2006.01)
   *C12P 7/06*    (2006.01)
   *C12N 9/42*    (2006.01)

(52) U.S. Cl. .................... 435/165; 435/41; 435/161; 435/209

(58) Field of Classification Search ................ None
   See application file for complete search history.

(56) References Cited

U.S. PATENT DOCUMENTS

| | | | |
|---|---|---|---|
| 2,140,189 A | 12/1938 | Mason | |
| 2,234,188 A | 3/1941 | Mason | |
| 3,212,939 A | 10/1965 | Hess et al. | |
| 3,707,436 A | 12/1972 | O'Connor et al. | |
| 3,817,786 A | 6/1974 | Algeo et al. | |
| 4,136,207 A | 1/1979 | Bender et al. | |
| 4,368,268 A | 1/1983 | Gong | |
| 4,490,468 A | 12/1984 | Gong | |
| 4,511,656 A | 4/1985 | Gong | |
| 4,520,105 A | 5/1985 | Sinner et al. | |
| 4,529,699 A | 7/1985 | Gerez et al. | |
| 4,600,590 A | 7/1986 | Dale | |
| 4,615,742 A | 10/1986 | Wright et al. | |
| 4,663,284 A | 5/1987 | Jefferies | |
| 4,731,329 A | 3/1988 | Lawford | |
| 4,812,410 A | 3/1989 | Lawford | |
| 4,816,399 A | 3/1989 | Lawford | |
| 4,840,903 A | 6/1989 | Wu | |
| 4,876,196 A | 10/1989 | Salzbrunn et al. | |
| 4,912,237 A | 3/1990 | Zeitsch et al. | |
| 4,964,995 A | 10/1990 | Chum et al. | |
| 5,000,000 A | 3/1991 | Ingram et al. | |
| 5,028,539 A | 7/1991 | Ingram et al. | |
| 5,047,332 A | 9/1991 | Chahal et al. | |
| 5,100,791 A | 3/1992 | Spindler et al. | |

(Continued)

*Primary Examiner*—Christopher R Tate
*Assistant Examiner*—Aaron J Kosar

(57) ABSTRACT

The invented process separates main components in lignocellulosic biomass, specifically hardwoods, softwoods into lignin and fractions of high purity sugars which are used for ethanol production. The invented process comprises of treatment stages at high temperature and high pressure with hydrochloric acid or sulfuric acid. Residual lignin and extractives in the cellulosic solid fraction are selectively removed by chemical treatments of sodium chlorite, anhydrous acetic acid, chlorine and chlorine dioxide to enhance the purity and biological conversion of cellulose to ethanol. The pre-hydrolysate generated from the acid treatment stage, containing xylose, arabinose, galactose, glucose and the purified cellulosic fraction are enzymatically hydrolyzed and fermented to produce ethanol. Significant amount of lignin from the process is recovered as a by-product.

2 Claims, 3 Drawing Sheets

GENERAL DIAGRAM OF THE MODULAR PROCESS CONVERTING
LIGNOCELLULOSIC BIOMASS TO ETHANOL AND CHEMICAL BY-PRODUCTS

U.S. PATENT DOCUMENTS

| | | |
|---|---|---|
| 5,328,562 A | 7/1994 | Rafferty et al. |
| 5,372,939 A | 12/1994 | Lastick et al. |
| 5,411,594 A | 5/1995 | Brelsfud |
| 5,424,417 A | 6/1995 | Torget et al. |
| 5,503,996 A | 4/1996 | Torget et al. |
| 5,514,583 A | 5/1996 | Picataggio et al. |
| 5,536,325 A | 7/1996 | Brink |
| 5,705,369 A | 1/1998 | Torget et al. |
| 5,712,133 A | 1/1998 | Picataggio et al. |
| 5,726,053 A | 3/1998 | Picataggio et al. |
| 5,730,837 A | 3/1998 | Black et al. |
| 5,785,852 A | 7/1998 | Rivard et al. |
| 5,798,237 A | 8/1998 | Picataggio et al. |
| 5,807,952 A | 9/1998 | Agblevor |
| 5,843,760 A | 12/1998 | Zhang et al. |
| 5,868,997 A | 2/1999 | Wyman |
| 5,879,463 A | 3/1999 | Proenca |
| 6,022,419 A | 2/2000 | Torget et al. |
| 6,172,272 B1 | 1/2001 | Shabtai et al. |
| 6,423,145 B1 | 7/2002 | Nguyen et al. |
| 6,498,029 B2 | 12/2002 | Keller et al. |
| 6,566,107 B1 | 5/2003 | Zhang et al. |
| 6,660,506 B2 | 12/2003 | Nguyen et al. |
| 6,719,908 B2 | 4/2004 | Hames |
| 6,737,258 B2 | 5/2004 | Hames et al. |
| 2007/0141693 A1* | 6/2007 | Berg et al. ............ 435/204 |

* cited by examiner

GENERAL DIAGRAM OF THE MODULAR PROCESS CONVERTING
LIGNOCELLULOSIC BIOMASS TO ETHANOL AND CHEMICAL BY-PRODUCTS

SIMPLIFIED PROCESS DIAGRAM OF SOFTWOOD LIGNOCELLULOSIC
FEEDSTOCK FOR PRODUCTION OF ETHANOL

SIMPLIFIED PROCESS DIAGRAM OF HARDWOOD LIGNOCELLULOSIC FEEDSTOCKS FOR PRODUCTION OF ETHANOL

INTEGRATED PROCESS FOR SEPARATION OF LIGNOCELLULOSIC COMPONENTS TO FERMENTABLE SUGARS FOR PRODUCTION OF ETHANOL AND CHEMICALS

This application claims priority to provisional application number U.S. 60/842,225 filed on Sep. 5, 2006.

This is a SUBSTITUTE SPECIFICATION for 11/700,718 filed on February, 2007.

DESCRIPTION

1. Field of the Invention

The present invention relates to the manufacture of principally ethanol. More specifically, it relates to a process for fractionating the major components in lignocellulosic material to fermentable sugars and for production of ethanol from hardwoods and softwoods. The process is very robust and agricultural biomass such as corn stover, grass and waste paper products can also be used as raw materials.

2. Background Art

Increasing demand for liquid fuels and higher cost of petroleum crude oil have encouraged new technologies to manufacture liquid fuel such as ethanol and chemicals from renewable biomass resources. It is desirable for the U.S. to transition to resources which are low cost, plentiful and renewable for its energy needs.

One of the most generally recognized fuel substitutes which could be made available in significant quantities is ethanol.

Today throughout most of the world, ethanol is produced through fermentation. In fermentation, yeast is added to a solution of simple sugars. Yeast is a small microorganism which uses the sugar as food, and in doing so, expels ethanol and carbon dioxide as byproducts. After fermentation, ethanol is further concentrated by distillation. Distillation towers capable of such separation and concentration are well-known in the art.

Industrial ethanol fermentation processes have generally been with grains or corn, but other biomass sources must be considered. Renewable resources, such as hardwood (beech, aspen, oak, gum, eucalyptus, etc.), softwood (pine, firs, spruce, etc.) from managed private and federal forests in the United States are abundant and sufficient to produce all of the country's needs for liquid fuel. Woody plant material typically is composed of 40-55% cellulose, 24-40% hemicelluloses, and 18-28% lignin. Cellulose is a polymer of D-glucose with beta linkages between each of about 10,000 glucose units. Hemicellulose is a polymer of sugars, primarily D-xylose with other pentoses and some hexoses with beta linkages. Lignin, a complex random polyphenolic, coats the bundles of cellulose fibers and binds them together to provide the wood with rigidity and resistance to breakdown. Cellulose, hemicelluloses and lignin make up 96-98% of the wood dry weight. The first operation of a bio-refinery is the separation of these components. Lignocellulose represents a low cost and abundantly available substrate for the preparation of sugars, which may be used alone or microbially fermented to produce alcohols and other industrial chemicals.

Among the techniques for the production of fuel grade ethanol from lignocellulosic biomass include the acid hydrolysis of cellulose and hemicelluloses. The hydrolyzed sugars are labile to the harsh hydrolysis conditions and may be degraded to unwanted or toxic byproducts. If exposed to acid for too long at elevated temperatures, the glucose derived from cellulose degrades into hydroxymethylfurfural, which can be further degraded into levulinic acid and formic acid. Xylose, a hemicellulose sugar, can be degraded into furfural and further to tars and other degradation products.

In order for acid to completely hydrolyze the cellulose and hemicelluloses in a lignocellulosic substrate, degradation of the sugars and formation of the toxic byproducts can not be avoided. On the other hand, to use conditions sufficiently gentle that significant degradation of sugars will not occur does not result in complete hydrolysis of substrate. Hemicelluloses are much more accessible and easier to be converted to sugars under milder hydrolysis conditions than cellulose.

Recently, attention has focused on enzymatic hydrolysis of cellulose with cellulase followed by fermentation of the resulting sugars to produce ethanol. Cellulase is an enzyme complex that includes three different types of enzymes involved in the saccharification of cellulose. The cellulase enzyme complex produced by *Trichoderma reesei* contains the enzymes named endoglucanase cellobiohydrolase and beta-glucosidase. The combined synergistic actions of these three enzymes in the cellulase preparation completely hydrolyse cellulose to D-glucose.

However, cellulase to a great extent cannot degrade cellulose in unpretreated lignocellulose because the hemicelluloses and lignin interfere with the access of the enzyme complex to the cellulose, probably due to their coating of the cellulose fibers. Furthermore, lignin itself can bind cellulase thereby rendering it inactive or less effective for digesting cellulose.

U.S. Pat. No. 3,212,932 Hess et al., discloses a multi-stage hydrolysis process in which ligno-cellulose is treated with mineral acid and subjected to high pressures of steam. U.S. Pat. Nos. 3,667,961 and 3,817,786 Algeo both disclose a process in which ligno-cellulose material, on a batch basis, is subject to very high pressure steam, and then released.

U.S. Pat. No. 4,136,207 assigned to Bender of Stake Technology Ltd disclosed a method of treating lignocellulose materials to produce ruminant feed. Ligno-cellulosic material such as aspen, poplar wood is mechanically compacted and then abruptly subjected to saturated steam at elevated pressure. The ligno-cellulosic material is cooked by the saturated steam at a given pressure of at least 200 psig and for a time of at least 15 seconds. Prior to discharge from the digester at the end of the cooking process, the ligno-cellulosic material is mechanically compacted and then subjected to rapid release of pressure and consequent cooling. When the feed is suddenly and abruptly subjected to the saturated steam, at elevated pressures and temperatures, it "relaxes" or de-compacts, permitting prompt and thorough steam penetration throughout the mass of the material.

U.S. Pat. No. 4,529,699 discloses a process for obtaining ethanol by continuous acid hydrolysis of cellulosic materials by providing a homogenized slurry of heated (160 to 250 Centigrade) cellulosic material continuously into a reactor, adding concentrated acid to the pressurized and heated cellulosic material to obtain hydrolysis, neutralizing and fermenting the resulting aqueous solution to obtain ethanol, and recovering resulting by-products of methanol, furfural, acetic acid and lignin.

A process for the production of sugars and optionally cellulose and lignin from lignocellulosic raw materials is disclosed in U.S. Pat. No. 4,520,105. The process entails subjecting vegetable materials to a chemical pretreatment with a mixture of water and lower aliphatic alcohols and ketones at 100 Centigrade to 190 Centigrade. for a period of from 4 hours to 2 minutes with control of the breakdown of the hemicellulose components followed by separation of residue and a subsequent chemical treatment with a similar solvent mixture at elevated temperatures for a period of from 6 hours to 2 minutes.

A process for rapid acid hydrolysis of lignocellulosic material is disclosed in U.S. Pat. No. 5,879,463. The process is a continuous process for acid hydrolysis of lignocellulosic material through which delignification and saccharification are carried out in a single reaction cycle employing a solubilizing organic solvent of lignin and a strong and extremely diluted inorganic acid to obtain highly concentrated recoveries of sugar.

U.S. Pat. No. 5,411,594 disclosed a hydrolysis process system for continuous hydrolysis saccharification of lignocellulosics in a two-stage plug-flow-reactor system. The primary final product is the combined hydrolysate sugars in a single solution, including pentose, hexose and glucose sugars, which are fermented into ethanol and Torula yeast. The secondary final solid product is an unhydrolyzed lignin solid.

A method of treating biomass material using a two-stage hydrolysis of lignocellulosic material is disclosed in U.S. Pat. No. 5,536,325. The conditions during the first stage is such as to hydrolyze or depolymerize the hemicellulosic component without substantial degradation of resulting monosaccharides and conditions during the second stage being such as to hydrolyze the cellulose to glucose without substantial degradation of the glucose. Hydrolysis in both stages are accomplished by the use of nitric acid, and the pH, retention time, and temperature in both stages are selected to maximize production of the desired monosaccharide or monosaccharides.

U.S. Pat. No. 6,022,419 discloses a multi-function process for hydrolysis and fractionation of lignocellulosic biomass to separate hemicellulosic sugars from other components such as extractives and proteins, solubilized lignin, cellulose, glucose derived from cellulose and insoluble lignin form the biomass by introducing a dilute acid into a continual shrinking bed reactor containing a lignocellulosic material at 94 to 160 Centigrade. for 10 to 120 minutes at a volumetric flow rate of 1 to 5 reactor volumes to solubilize extractives, lignin, and protein by keeping the solid-to-liquid ratio constant throughout the solubilization process.

A process, disclosed in U.S. Pat. No. 6,660,506 of converting lignocellulosic biomass to ethanol, comprising hydrolyzing lignocellulosic materials by subjecting dried lignocellulosic material in a reactor to a catalyst comprised of a dilute solution of a strong acid and a metal salt to lower the activation energy (i.e., the temperature) of cellulose hydrolysis and ultimately obtain higher sugar yields.

U.S. Pat. No. 4,600,590 disclosed a process in which cellulose is treated to increase its chemical and biological reactivity by contacting cellulose-containing materials in a pressure vessel with liquid ammonia, and under the vapor pressure of liquid ammonia at ambient temperature. The mixture is stirred for a period of time sufficient for the ammonia to wet and swell the cellulose-containing material.

The best known of the liquid explosion processes is the so called "Masonite" process which is described in U.S. Pat. No. 2,140,189, to W. H. Mason. In the Masonite process, woodchips or similar cellulosic materials are pressurized by steam to pressures as high as 1000 psig (6.9 MPa). Upon sudden discharge of the woodchip/water/steam mixture from the pressurizer, the water trapped within the interstices of the woodchips flashes to steam and provides the necessary energy to produce a well defibrated pulp mass. The high temperatures associated with the injected steam (saturated 1000 psig steam, for instance, has a temperature of 285 Centigrade) are significantly higher than the softening range of cellulose (determined to be between 223 Centigrade and 253 Centigrade. Thus, when the cellulose is heated to 285 Centigrade and exploded, the softened cellulose fibers are considerably damaged and fragmented by the force of the explosion. The high temperatures of the Masonite process also induce hydrolytic attack of the cellulose, causing further weakening and fiber degradation. The hydrolytic attack can be partially ameliorated by preimpregnating the woodchips with alkalis prior to explosion as described in U.S. Pat. No. 2,234,188 to H. W. Morgan.

In its simplest form, explosion hydrolysis is carried out without any chemicals or additives but catalysts can be used. Explosion hydrolysis was widely practiced to produce hardboard by the Masonite process. Hardboard made by the Masonite process was bonded entirely with natural resins produced by the process.

U.S. Pat. No. 5,328,562 described an energy efficient process for hydrolyzing lignocellulosic materials where hydrolysis is performed using a saturated steam carrier for the lignocellulosic material in a first stage and continues into a second stage using a superheated steam.

U.S. Pat. No. 6,660,506 disclosed a two-stage fermentation process which incorporates yeast recycle in the first-stage liquid fermentors. The process enables the yeast to achieve 90% ethanol yield from fermentable sugars without the need for detoxification of the hydrolysate liquor. This adaptation method also reduces nutrient requirements.

Substantial hurdles must be overcome before a typical cellulosic feedstock can be utilized effectively as a substrate for the fermentative production of ethanol. Whereas microorganisms are known that can efficiently ferment the glucose component in cellulose, conversion of the xylose in the hemicellulose fraction to ethanol has been difficult.

*Zymomonas mobilis* is a bacterium that has been utilized as a natural fermentative agent in the production of alcoholic beverages. Comparative performance trials have suggested that *Zymomonas* may become an important industrial ethanol-producing microorganism because of its 5-10% higher yield and up to 5-fold higher productivity compared to traditional yeast fermentations. Because of its potential value, several processes based on the use of *Zymomonas* for production of industrial ethanol from glucose-based feedstocks have been disclosed in U.S. Pat. Nos. 4,731,329, 4,812,410, 4,816,399, and 4,876,196.

While *Zymomonas* may become an important ethanol-producing microorganism from glucose-based feedstocks, its substrate utilization range is restricted to glucose, sucrose and fructose and, as such, it is not naturally suited for fermentation of the xylose and arabinose components in cellulosic feedstocks. *Zymomonas* is naturally unable to ferment the xylose in cellulosic biomass because it lacks the essential pentose metabolism pathways. Thus, genetic engineering attempts have been made to enhance ethanol production by fermentation by transferring genes from one species to another (U.S. Pat. Nos. 5,000,000 and 5,028,539).

U.S. Pat. No. 5,514,583 disclosed the xylose-fermenting *Z. mobilis* has been developed by introduction and expression of four genes encoding xylose-assimilating enzymes, xylose isomerase and xylulokinase as well as pentose-phosphate pathway enzymes, transaldolase and transketolase. U.S. Pat. No. 6,566,107 disclosed *Zymomonas* mobilis or its derivative capable of producing ethanol upon fermentation of a carbohydrate medium containing xylose to provide enhanced xylose utilization and enhanced ethanol process yield.

U.S. Pat. No. 5,047,332 described an integrated process for the production of food, feed and fuel from biomass such as lignocellulosic materials, e.g. forest biomass; agricultural residues; or manures. The feed is pretreated and thereafter is fractionated into cellulose, lignin and hemicelluloses. New mutants are disclosed which include *Chaetomium* cellulolyticum, *Aspergillus* sp., *Penicillum* sp. and *Tricoderma reesei*. With these new mutants and also known fungi including *Pleurotus sajor-caju* and other *Pleurotus* spp. unfractionated biomass is converted into feed. The same treatment can also be applied to hemicelluloses, and cellullose. Cellulose can also be hydrolyzed by a cellulase-system prepared from cellulose and *Tricoderma* reesei to prepare glucose which can be converted to alcohol with *Saccharomyces cerevisiae*, *Kluyveromyces* spp. and *Zymomonas mobilis*.

U.S. Pat. No. 4,663,284 discloses a process for producing ethanol from D-xylose by fermentation with xylose metabolizing yeasts, wherein small quantities of glucose are added to the fermentation medium during the fermentation process; however, the process is not an enzyme mediated process. Yeast strains can ferment xylose if oxygen is allowed to be present in the fermentation. The process further disclose that the addition of glucose to these oxygen mediated fermentations improves the yield of the fermentation.

U.S. Pat. No. 4,511,656 pertains to a method for producing ethanol directly from D-xylose by yeast mutants. The process further provides for directly and simultaneously obtaining ethanol from a mixture of cellulose and hemicelluloses through yeast fermentation of D-glucose and D-xylose. In addition to oxygen being required, no enzymes are used and cellulose is not fermented.

In U.S. Pat. No. 4,490,468 to Gong et al., there is described an anaerobic fermentation of xylulose previously obtained by isomerization of xylose; however, the process is not combined in any way with the fermentation of cellulose.

U.S. Pat. No. 4,368,268 to Gong relates to a process for the production of ethanol from xylulose. The process includes isomerizing the xylose to xylulose and fermenting the xylulose to ethanol. Essentially, this process is the fermentation of xylose and other sugars in hemicellulose hydrolysates by mutant strains of yeast, either aerobically or anaerobically. The cellulose is not soluble and must be enzymatically digested to produce soluble sugars.

U.S. Pat. No. 4,385,117 pertains to a process for continuously producing ethanol such that a substrate can be added to a fermentation and the ethanol can be removed therefrom during a fermentation comprising an aqueous nutrient medium containing the substrate greater than one percent (w/v) wherein the substrate is starch, pectin, monosaccharides and disaccharides, under anaerobic and thermophilic conditions to the fermentation action of *Thermoanaerobacter ethanolicus*.

U.S. Pat. No. 4,840,903 discloses a process for the production of ethanol by a fungal strain capable of slowly degrading and fermenting cellulose, xylose, and a number of other sugars. Like simultaneous saccharification and fermentation (SSF) of cellulose, cellulase enzymes were added to the fermentations to produce glucose from cellulose; however, fungal strains take much longer to grow and ferment, and these longer lengths of time or slow rates are unacceptable for industrial purposes.

U.S. Pat. No. 5,372,939 disclosed a process using combined enzyme mediated fermentation of cellulose and xylose to ethanol by *Schizosaccharoyces pombe*, cellulase, beta-glucosidase, and xylose isomerase. This process relates to a process that combines a simultaneous saccharification and fermentation (SSF) process and a simultaneous fermentation and isomerization of xylose (SFIX) process to provide a simpler and reduced cost process for producing ethanol. In particular, this invention pertains to producing ethanol from a mixed stream of xylose and cellulose and includes fermenting the mixed stream using a cellulase and xylose isomerase enzyme. The fermentations are conducted under totally anaerobic The fermenters are continuously controlled to maintain a pH range between about 5.5 and about 6.0, preferably at a pH of 5.75.

U.S. Pat. No. 5,100,791 disclosed simultaneous saccharification and fermentation (SSF) using cellobiose fermenting yeast *Brettanomyces custersii* for producing ethanol from plant biomass substrate including hydrolysates of cellulose and hemicelluloses. Hemicellulose is likewise readily and easily converted to its various hydrolysate products by mild acid hydrolysis or enzymatic hydrolysis treatment and the resultant products include various pentoses (xylose and arabinose being the main derivatives), hexoses (mannose and galactose), and sugar acids. By far, D-xylose is the major sugar in hemicellulose hydrolysate and constitutes approximately 60-80 percent of the total hydrolysates produced therefrom.

In a simultaneous saccharification fermentation process, saccharification involves the breakdown of cellulose into simpler sugars by a cellulase enzyme, *Brettanomyces custersii* displays a high ethanol tolerance (namely, about 94 grams per liter) and a high temperature tolerance range (30C-37 Centigrade), gives high ethanol conversion rates and yields and capable of producing high concentrations of ethanol from a wide variety of six carbon sugars derived from cellulose and hemicelluloses. B. Custersii ferments disaccharides such as sucrose, maltose, lactose and cellobiose (but excluding melibiose and trehalose), polysaccharides such as starch and hexoses such as glucose, fructose, sorbose, mannose and galatose. The pH of the fermentation medium can range from a pH of about 3.5 to a pH of 6.0. The temperature of the fermentation process can also vary considerably from about 28 Centigrade to about 42 Centigrade.

It appears that hemicelluloses and lignin interfere with the access of the enzyme complex to the cellulose, probably due to their coating of the cellulose fibers. Furthermore, lignin itself can bind cellulase thereby rendering it inactive or less effective for digesting cellulose. U.S. Pat. No. 6,737,258 described a method for selective removal of fermentation inhibitors such as lignin derived guaiacyl or syringyl phenols in a biomass hydrolyzate by contacting a metal oxide having an affinity for these functional groups.

U.S. Pat. No. 4,912,237 disclosed a process for producing furfural from a feed suspension of pentosan-containing organic raw materials in dilute sulfuric acid.

U.S. Pat. No. 6,172,272 disclosed a high-yield process for converting lignin into oxygenated gasoline of high quality. The process is a two-stage catalytic reaction process that produces a reformulated, partially oxygenated gasoline product with a controlled amount of aromatics.

OBJECTS OF THE INVENTION

A principal object of the present invention is a conversion process of hardwoods and softwoods for the production of ethanol. This process is cost effective, robust and applicable to wood as well as other lignocellulosic feedstocks.

Another principal object of the present invention is a potent manufacturing process for removing residual condensed lignin and extractives from the cellulose hence improving the biological reactivity of cellulose in the manufacturing of ethanol.

Other objects and advantages of the invention will become apparent from the following description of the preferred embodiment.

SUMMARY OF THE INVENTION

After the prehydrolysate containing primarily fermentable sugars from hemicelluloses is separated, the pre-hydrolyzed lignocellulose substrate is washed in a 3-stage counter-current washer and treated chemically by first extracting lignin with sodium hydroxide, followed by chlorine and chlorine dioxide solution and sodium chlorite and anhydrous acetic acid solution, to remove the extractives and residual lignin. The filtrates from the counter-current washers after the chemical treatments with caustic and sodium chlorite-anhydrous acetic acid can be combined and evaporated to produce lignin-based chemicals or incinerated to generate power/steam for process uses. The remaining cellulose, essentially free of lignin and extractives which are detrimental and toxic to fermentation by bacteria/yeast and enzymatic saccharification, is subjected to subsequent operations of saccharification/fermentation and distillation to produce ethanol.

The invention is a versatile and effective process using proven technologies to produce ethanol from the most abundant and renewable wood biomass resources.

The process is illustrated in FIGS. 1 to 3.

DESCRIPTION OF THE PREFERRED EMBODIMENT

Figure 1:
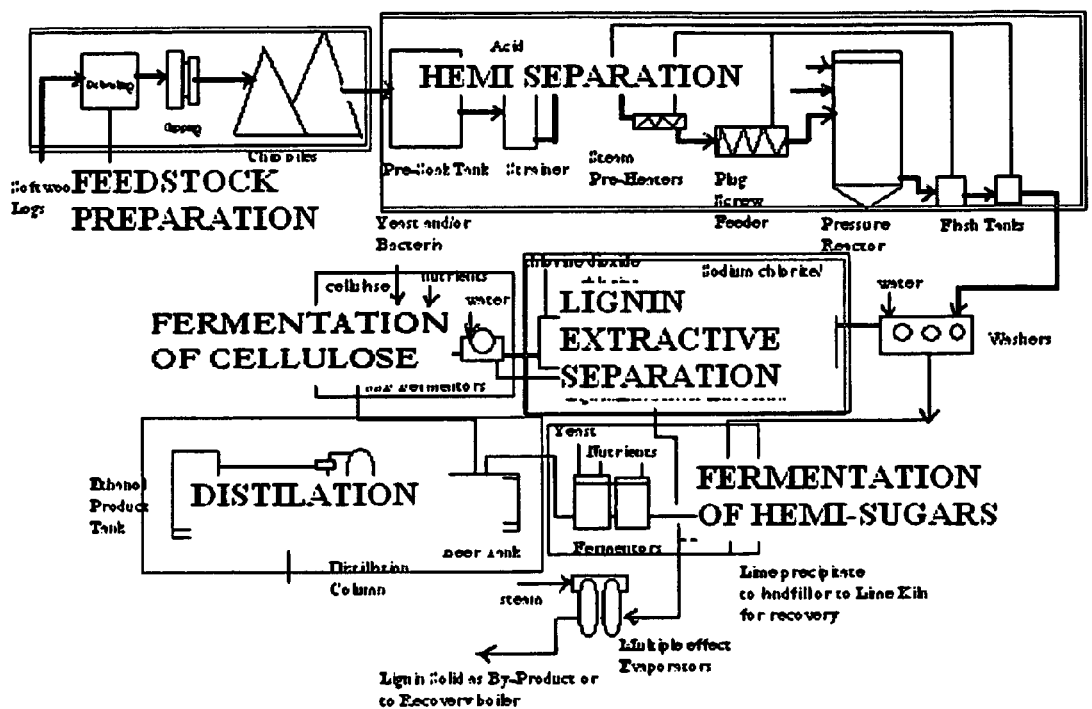
FIG. 1 is a general diagram of the modular process converting wood biomass to ethanol. The process consists of several modules: Physical preparation of lignocellulosic wood biomass, Hemi-Prehydrolysis, Lignin/Extractives Separation, Saccharification and Fermentation of Cellulose, Fermentation of Hemi-sugars, Distillation, and Recovery of by-products.
Figure 2:
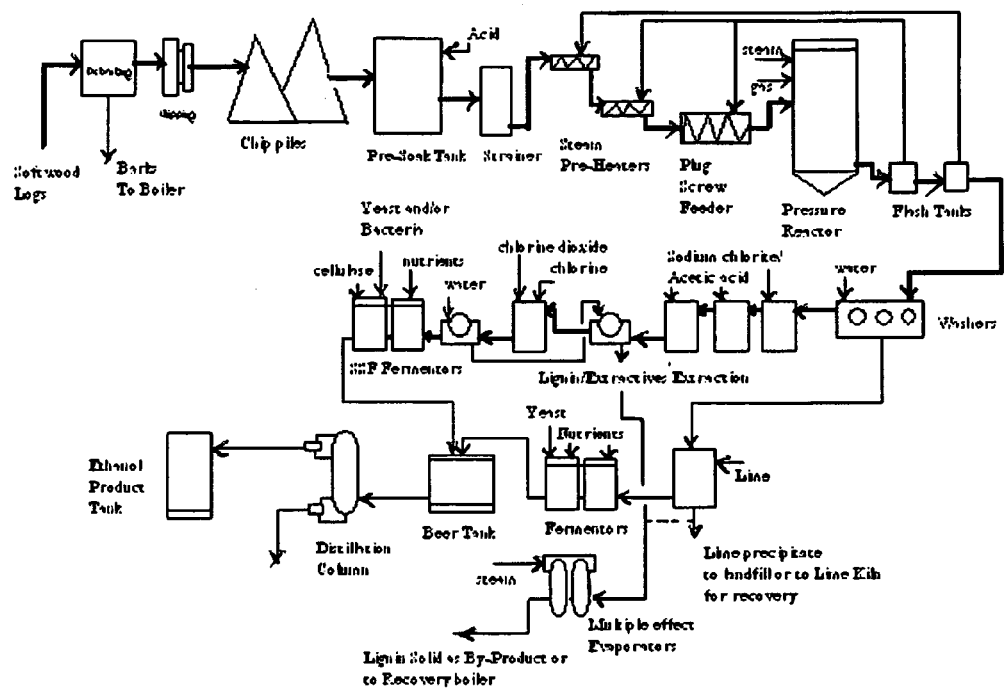
FIG. 2 shows the process diagram for difficult-to-remove lignin and high extractive softwoods.
Figure 3:
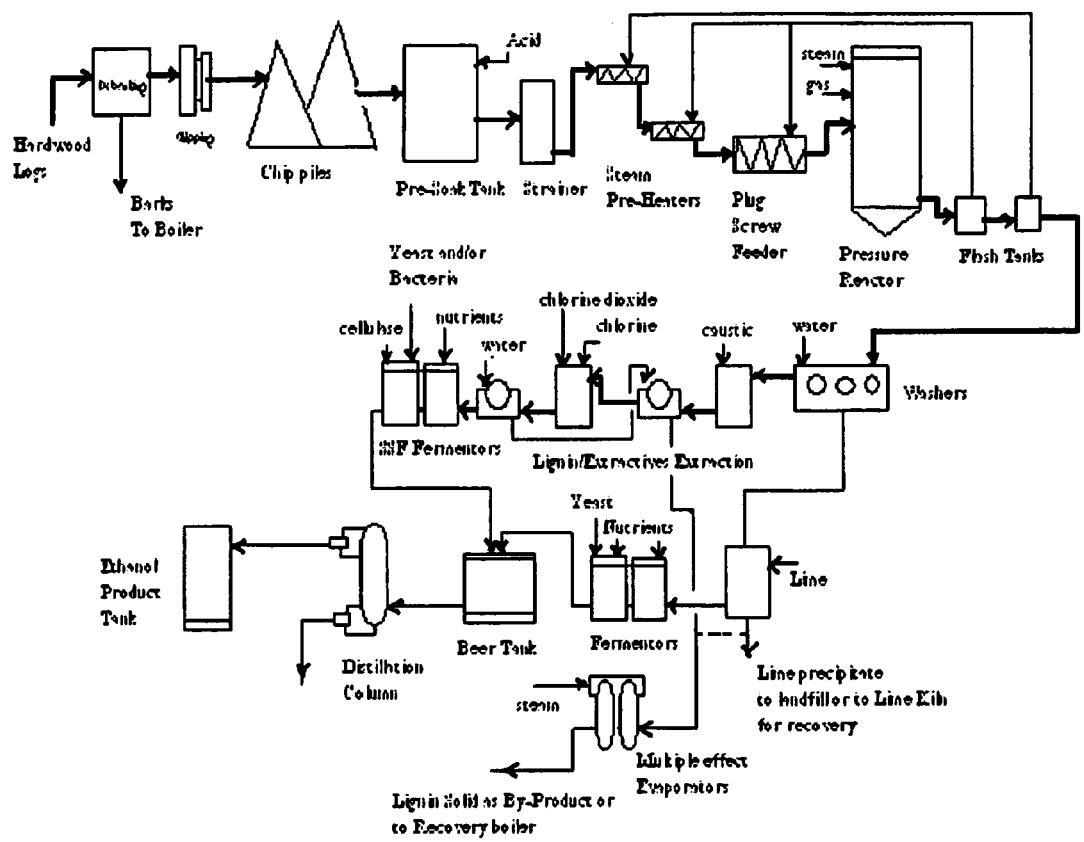
FIG. 3 shows the process diagram for hardwoods containing less condensed residual lignin and extractives.

The invention is a process to manufacture ethanol from lignocellulosic materials, especially for the abundantly available hardwoods, softwoods, and not excluding other biomass sources such as corn stover, sugarcane, grass, waste papers, recycled papers. The claimed process comprises the following stages aimed primarily to separate the three major components in wood namely hemicelluloses, cellulose and lignin, hence increase the efficiency and cost effectiveness of the ethanol manufacturing process. The claimed invention fractionates wood and lignocellulosic biomass into three product streams including lignin, a prehydrolysate containing fermentable hemicellulosic sugars and a very pure cellulosic solid. A number of known bio-conversion technologies can then be applied to produce ethanol from the fermentable sugars and the cellulosic solid produced from this invented process.

The integral, continuous and modular process consists essentially of the following preferred treatments:

Chip wood into chips of ¼ to 1 inch with thickness of approximately ¼ inch, similar to wood chips used in the pulp and paper industry. Wood chips at their natural moisture content (about 40-50% solids consistency) are sent to a pre-soak tank where up to 5% (on oven dried weight basis of biomass) acid (sulfuric acid, or hydrochloric acid, or nitric acid) is added to achieve a pH value of about 2-3. After approximately 1 to 4 hours, the acid-presoaked chips are centrifuged to remove excess acid and effect a solids consistency of about 30-35%. The chips are then conveyed and heated with blow tank flash steam in steam mixers and screw fed into a pressurized reactor. Direct live steam and inert gas (such as carbon dioxide, air, nitrogen, oxygen) can be added to raise the reactor temperature and pressure. The reaction time is kept for up to 30 minutes at 190 Centigrade to 300 Centigrade and 250-1000 psig pressure. The products from the high pressure reactor are released (blown) under high pressure into a series of blow tanks. Flash steam from the blow tanks are recovered and applied to heat the feed in pre-heat steam mixers. The product from the last blow tank is pressed to separate the pre-hydrolysate liquor and solids, then washed in a series of counter-current washers to recover the hydrolyzed sugars. Water usage should be limited to a dilution factor of 2-3 (dilution factor is defined as DF=(tons of water−tons of water in solid)/tons of solid) or less, so that filtrate from the washer contains high concentration of fermentable sugars such as xylose, arabinose, etc. from hemicelluloses. Lime is added to the pre-hydrolysates in a decanter tank with approximately 3-4 hour residence time to neutralize to a pH 8-10 and precipitate extractives, toxic compounds; after neutralization the pre-hydrolysate containing sugars from hemicelluloses is ready for fermentation. The solids remained from the pressurized pre-hydrolysis stage contain primarily lignin, cellulose and extractives. Lignin insome softwood species could be highly condensed, difficult to remove from the cellulosic solids and negatively affect the biological activities of enzyme and yeast in the subsequent enzymatic saccharifiation and yeast/bacteria fermentation.

After the pre-hydrolysis stage, there are two preferred options for extracting and further delignifying the lignocellulosic solids.

a. For highly condensed and significant quantity of lignin: lignocellulosic solids are charged into a series of two- to four-stage continuous co-current packed bed reactors. In each stage, a 1% to a maximum 10% charge (based on wood solids) of highly selective delignifying chemical agents sodium chlorite/anhydrous acetic acid (about 5/1 ratio) solution is added in a stock mixer before the reactor. Alternatively, in place of the sodium chlorite and anhydrous acetic acid mixture, chlorine/chlorine dioxide (about 70/30 ratio) solution, or calcium hypochlorite solution, can be used. The temperature of the reactor is maintained in the range of 120-180 Fahrenheit; the residence time of the reactor is 3-4 hours. After exiting from the first stage reactor, the solids are separated from the filtrate without washing. The solids are sent to the subsequent stages, also packed bed reactors, where fresh solutions of sodium chlorite and anhydrous acetic acid are added at the beginning of each stage. Process conditions such as temperature, pressure, and residence time in these subsequent stages are similar to those in the first stage.

b. For less condensed and extractable lignin, the substrate solids are first treated with caustic at moderate temperature. Caustic extraction stage is to solubilize color components and soluble oxidized lignin. This stage is employed to reduce the amount of more expensive oxidizing chemicals, chlorine, chlorine dioxide, sodium chlorite/anhydrous acetic acid, calcium/sodium hypochlorite, in subsequent delignification stages. Hot caustic extraction also removes alkali soluble polysaccharide fraction (hemicelluloses). Thus temperature should not exceed 150 Fahrenheit or 65 Centigrade. Caustic charge is typically 2-10% on solids, temperature is 80-150 Fahrenheit, residence time is 1-3 hours. The amount of caustic charge is controlled to obtain an extraction pH between 10.5-11. After caustic extraction, the solid is washed with water and/or filtrate from the chlorine/chlorine dioxide (or sodium chlorite/anhydrous acetic acid stage washer filtrate. Chlorine/chlorine dioxide are charged (1:1 to 1.5:1, based on residual lignin content, often designated as kappa number, ROE number, chlorine number, permanganate number) to delignify and de-resinate the solids. Chlorine dioxide charge should be 30-50% of the total equivalent chlorine charge. The sequence of chemical application is chlorine dioxide and then chlorine to achieve maximum effect of oxidation. Temperature is 80-120 Fahrenheit, residence time is 1 hour-3 hours, solids consistency is 3-10%. After chlorine dioxide/chlorine stage, the remaining solid is washed and the filtrate can be used in the caustic extraction washer or mixed with other filtrates containing lignin, degradation products for evaporation and recovery or further converted to chemicals and hydrocarbon fuel. The solids remaining from the reaction contain primarily cellulose and the filtrate liquid contains lignin, extractives, methanol, acetic acid, color, etc. Solids and liquid are separated and the solids are washed in a series of counter-current washers.

The cellulose substrate, now free of most residual toxic components categorized as lignin and extractives can be converted to glucose by cellulose enzymatic hydrolysis.

Or the cellulose can be converted directly to ethanol by adding cellulase and yeast or bacteria together in a simultaneous saccharification fermentation (SSF)

Or a mild dilute acid hydrolysis stage under moderate temperature can be used to convert the cellulose into fermentable glucose. High conversion yield to glucose, better than 90% is expected with the pure cellulose substrate, since kinetics of degradation reactions can be controlled with temperature, time and acid concentration.

Similarly, the two product streams as described in this process containing glucose (hydrolysate) and xylose/arabinose (pre-hydrolysate) can be fermented separately, or can be combined to be fermented together to produce ethanol.

Process streams and filtrates containing lignin, can be concentrated in multiple effect evaporators and converted to hydrocarbon fuel or used as a by-product, or burned to generate power and steam for process uses.

EXAMPLES

Major hurdles in the development of commercially feasible biomass-to-ethanol processes are the high cost of biomass raw material and the need to develop effective pretreatment methods that result in high hemicellulose sugar yield and high enzymatic cellulose digestibility. This claimed process can efficiently convert wood, the most abundant and low cost biomass to fermentable sugars by effectively removing highly condensed lignin and extractives which are inhibitors in most fermentations.

In general, the process of invention for converting lignocellulosic biomass to ethanol employs: a high pressure/high temperature, short residence time pre-hydrolysis stage that hydrolyzes the acid-impregnated lignocellulosic biomass to convert hemicelluloses to fermentable sugars; a counter-current washing/extraction to recover over 95% of soluble sugars with minimal dilution of sugar solution; followed by sequential extraction stages for the removal of residual lignin, extractives with caustic extraction, and potent chemicals sodium chlorite/anhydrous acetic acid or chlorine/chorine dioxide to yield a solid fraction of pure cellulose.

The cellulose is fermented with cellulase enzyme to glucose which can be combined with the prehydrolyzed sugars (xylose, galactose, mannose, etc.) and fermented to ethanol which is further concentrated to pure ethanol in a distillation operation.

Example 1

In this example, the biomass feedstock of hardwood (oak, gum, aspen) sawdust and chips (¼ to ¾ inch) at typically 50% to 60% moisture content is pre-soaked with an acid solution which is pre-heated to about 85 Centigrade with 30 psig saturated steam from the blow tank for approximately 60 minutes in the acid impregnator.

Various types of acids used in the prehydrolysis stage can be added to the impregnator. If gaseous sulfur dioxide is used, no water is added. If another strong acid such as sulfuric, hydrochloric, or nitric or any strong acid which effect pH values below about 3, is used, a dilute solution of one of these acids is heated with low pressure flash steam from about 40. to about 80 Centigrade before adding to the impregnator Because of the low cost and relative ease of handling, sulfuric acid is selected in the dilute acid hydrolysis process. Acid impregnation is achieved by soaking the biomass in dilute acid solution, under elevated temperature and pressure. To thoroughly soak the biomass in the acid solution, a residence time of about 1 to 2 hours is required. The acid-soaked feedstock is drained or squeezed to about 35% solids upon exiting the impregnator. The feedstock is further dewatered to about 40% to about 60% solids using a dryer or a centrifuge The sulfuric acid concentration of the liquid in the biomass prior to feeding into the first-stage hydrolyzer is in the range of from about 0.2% to about 4.0% by weight.

Excess acid solution is then removed from the biomass, by pressing via a screw press. Most continuous biomass hydrolyzers, such as the Sunds Hydrolyzer, the Pandia Reactor, the Stake Reactor, employ screw feeders to feed biomass into the reactor under pressure. The pressure in the screw feeders can reach as high as 1,200 psig. At this pressure the solid content is increased to about 70%.

The acid-impregnated biomass is fed into the hydrolyzer and steam is directly injected into the hydrolyzer in order to heat the biomass to the desired temperature of 250 to 280 Centigrade for a period of from about 1 to 30 minutes. The hydrolysate slurry is then discharged into a flash tank operating at a temperature of from about 120 to about 140 Centigrade for a period of from about 20 minutes to about 2 hours to hydrolyze most of the soluble oligosaccharides to monomeric sugars. The hydrolysate slurry from the first tank is then flashed into a second flash tank operating at a temperature of about 95 Centigrade.

In excess of 95% of soluble sugars from the hydrolysate slurry are recovered by the counter-current washers (this may be a screw-conveyor extractor or a vacuum belt extractor). The hydrolysate solids is washed with warm/hot water at a temperature of from about 40 to 70 Centigrade, on a 2- or 3-stage countercurrent vacuum washer, wherein the water is used in a ratio of from about 2:1 to 4:1 (equivalent to a Dilution Factor of 3) for liquid-to-insoluble solids.

Digestible sugars and the hemicellulose oligomers remain in solution, while the lignin and cellulose are filterable solids. The solids at about 12% to 15% solids, are conveyed to the caustic extraction and delignification/extractive removal stages.

The acidic prehydrolysate is neutralized. Alkali (or lime) is added to the filtrate to bring the pH to about 5. The precipitates (mostly gypsum) are filtered out and the filtrate is forwarded to the fermentor.

Lignin and Extractives Removal

About 6% (based on dry-weight of solids) of sodium hydroxide is added to the steam mixer where the chemicals, steam and solids are heated to a temperature of 50 to 60 Centigrade and gravity fed into a down flow tower to give a residence time of 2-4 hours. About 70-80% of lignin in the substrate are solubilized in the caustic extraction and 20% to 30% of more condensed lignin remain. The product slurry exiting the caustic extraction tower is gravity fed into a single stage vacuum rotary vacuum washer where hot water or filtrate from the chlorination/chlorine dioxide stage at a ratio 5:1 to the solids is used to wash the soluble lignin from the solids.

Approximately 5% total chlorine, of which 70% is elemental chlorine (chlorine liquid can be used) and 30% is chlorine dioxide (about 0.6%) on weight of solids, are added and mixed to the washed solids. Steam is added to raise the temperature to about 40 Centigrade. The pH is controlled to 2-3 by adding either acid or caustic to the mixture. Water or preferably filtrate from the chlorine/chlorine dioxide washer is added to get a solids consistency of 3-4% by weight. The residence time of this stage is approximately 30 to 60 minutes.

After chlorination/chlorine dioxide stage, the solids again is washed with fresh hot water. Wash water usage is controlled to a dilution factor of 3, at exit stock consistency of 12%. Excess chlorination washer filtrate containing chlorinated lignin, phenols, extractives, after satisfying the dilution and process dilution uses, are mixed with filtrate from the caustic extraction stage washer. The combined filtrates can be evaporated to high solids concentration, 50-70% solids, and can be used to convert to chemicals, fuels or incinerated for steam and power. Cellulose degradation in the caustic and chlorination extraction/delignification stages are minimal, typically from 1% to 3%. The remaining solid is pure cellulose, free of lignin, wood extractives, and hemicelluloses.

Ethanol fermentation is carried out separately for hemicellulose sugars and cellulose such as described below.

Prehydrolysate Fermentation:

The pH-adjusted and filtered extract from the countercurrent extractor is cooled to about 30 to about 40 Centigrade depending upon yeast strain and adaptation, and fed to the bottom of the fermentor. The fermentor has a residence time of about 15-20 hours. Air is sparged into the bottom to promote some yeast growth. The fermentor is equipped with a mixer to keep the yeast cells in suspension. Corn steep liquor and ammonium sulfate may be added as nutrients to the feed stream to promote yeast growth. The fermentor may be seeded with one or a mixed culture of hexose-fermenting yeast and xylose-fermenting yeast.

Cellulose Saccharification and Fermentation

Alkali such as lime or ammonia is added to the hydrolysate slurry to adjust the pH to about 4.5. The slurry is cooled to about 32 to 42 Centigrade depending upon yeast strain and adaptation method. Thereafter, the slurry is fed into the top of the fermentor of the 2 fermentor train. Cellulase is added mainly in the first fermentor. Broth exiting the first fermentor at the bottom is pumped to the top of the second fermentor. Both fermentors are equipped with mixers to keep the insoluble solids and yeast cells in suspension. The residence time in each fermentor is about 8 to 10 hours. The fermentation broth is then pumped into a beer well, which serves as a surge tank for distillation systems.

Distillation

Ethanol is recovered from the beer by conventional distillation methods. The trays of the beer column are designed to handle the insoluble solids. Pure ethanol is recovered at the top condenser and the bottom stillage can be used as animal feedstuff or incinerated.

Insoluble Solids Recovery

The beer column bottom stream is centrifuged to recover most of the suspended solids. The centrifuge cake is further dewatered to approximately 50% total solids using a press (filter press, belt press or screw press) before being sent to the biomass boiler.

Example 2

In this example the feedstock is white and brown waste papers.

The shredded waste paper mixture consists of 40% white bond paper and 60% brown carton, box, clippings, etc. The mixture is disintegrated in a repulper where plastic, wires, dirt, rock are removed. The stock mixture exiting the repulper at approximately 3-4% consistency are cleaned further with centri-cleaners to further remove dirt and sand. After cleaning, the mixture is chemically treated with 2-stage sodium chlorite/anhydrous acetic acid to remove lignin and extractives. Total charges in two stages are 5%, which is about 1.1 times the lignin content of the mixture. The ratio by weight of sodium chlorite to anhydrous acetic acid is maintained at 5:1 in both stages.

The temperature of the reactor is maintained in the range of 120-180 Fahrenheit; and the residence time of the reactor is 3-4 hours. After exiting from the first stage reactor, the solid is separated from the filtrate without washing. The solid is sent to the subsequent stages, where fresh solution of sodium chlorite, acetic acid anhydrous is added at the beginning of each stage. Process conditions such as temperature, pressure, and residence time are identical to the first stage.

The product slurry exiting the second reactor tower is gravity fed into a single stage vacuum rotary vacuum washer where hot water or filtrate from the chlorination filtrate at a ratio 5:1 to the solid is used.

Approximately 2% total chlorine, of which 70% is elemental chlorine (chlorine liquid can be used) and 30% is chlorine dioxide (about 0.6%) on weight of solids, are added and mixed to the washed solids. Steam is added to raise the temperature to about 40 Centigrade. The pH is controlled to 2-3 by adding either acid or caustic to the mixture. Water or preferably filtrate from the chlorine washer is added to get a solids content of 3-4% by weight. The residence time of this stage is approximately 30 to 60 minutes.

After chlorination/chlorine dioxide stage, the stock mixture again is washed with fresh warm water. Amount of water usage in the washing stage is controlled to a dilution factor of 3, at exit consistency of 12%. Excess washer filtrate containing chlorinated lignin, phenols, extractives, after satisfying the dilution and process uses, are mixed with caustic extraction stage washer filtrate. The combined filtrates can be evaporated to high solids concentration, 50-60% solids, and can be used to convert to chemicals, fuels or incinerated for steam and power. Cellulose degradation in the caustic and chlorination extraction/delignification stages are minimal, typically from 1% to 3% yield loss. The remaining solid is pure cellulose, free of lignin, wood extractives, and hemicelluloses.

Cellulose Saccharification and Fermentation

Alkali such as lime or ammonia is added to the hydrolysate slurry to adjust the pH to about 4.5. The slurry is cooled to about 32 to 42 Centigrade depending upon yeast strain and adaptation method. Thereafter, the slurry is fed into the top of the fermentor of the 2 fermentor train. Cellulase is added mainly in the first fermentor. Broth exiting the first fermentor at the bottom is pumped to the top of the second fermentor.

Both fermentors are equipped with mixers to keep the insoluble solids and yeast cells in suspension. The residence time in each fermentor is about 8 to 10 hours. The fermentation broth is then pumped into a beer well, which serves as a surge tank for distillation systems.

Subsequent steps for lignin and by-product recovery and ethanol distillation are similar to those described in example 1.

Example 3

In this example, mixture of feedstock of hardwood (oak, gum, aspen) and softwood (pine, spruce, firs) sawdust and chips (¼ to ¾ inch) at typically 50% to 60% moisture content is pre-soaked with an acid solution which is pre-heated to about 85 Centigrade with 30 psig saturated steam from the blow tank for approximately 60 minutes in the acid impregnator.

A dilute solution sulfuric acid is heated with low pressure flash steam from about 40 to about 80 Centigrade. before adding to the impregnator to affect a pH of 3 or below. To thoroughly soak the biomass in the acid solution, a residence time of about 1 to 2 hours is required. The acid-soaked feedstock is drained or squeezed to about 35% solids upon exiting the impregnator. The feedstock is further dewatered to about 40% to about 60% solids using a centrifuge. The sulfuric acid concentration of the liquid in the biomass prior to feeding into the first-stage hydrolyzer is in the range of from about 0.2% to about 4.0% by weight.

Excess acid solution is then removed from the biomass, normally by pressing via a screw press. Most continuous biomass hydrolyzers employ screw feeders to feed biomass into the reactor under pressure. The pressure in the screw feeders can reach as high as 1,200 psig.

The acid-impregnated biomass is fed into the hydrolyzer and steam is directly injected into the hydrolyzer in order to heat the biomass to the desired temperature of 250 to 280 Centigrade for a period of from about 1 to 30 minutes. The hydrolysate slurry is then discharged into a flash tank operating at a temperature of about 140 Centigrade for a period of from about 20 minutes to about 2 hours to hydrolyze most of the soluble oligosaccharides to monomeric sugars. The hydrolysate slurry from the first tank is then flashed into a second flash tank operating at a temperature of about 95 Centigrade.

In excess of 95% of soluble sugars from the hydrolysate slurry are recovered by the counter-current washers. The hydrolysate solids is washed with warm/hot water at a temperature of from about 40 to 70 Centigrade, on a 2- or 3-stage countercurrent vacuum washer, wherein the water is used in a ratio of from about 2:1 to 4:1 (equivalent to a Dilution Factor of 3) for liquid-to-insoluble solids.

Digestible sugars and the hemicellulose oligomers remain in solution, while the lignin and cellulose are filterable solids. The solids is at about 12% to 15% solids, and conveyed to the caustic extraction stage.

The acidic prehydrolysate is neutralized. Alkali (lime) is added to the filtrate to bring the pH to about 5. The precipitates (mostly gypsum) are filtered out and the filtrate is forwarded to the fermentor.

Lignin and Extractives Removal

About 5% (based on dry-weight of solids) of sodium hydroxide is added to the steam mixer where the chemicals, steam and solids are heated to a temperature of 50 to 60 Centigrade and gravity fed into a down flow tower to give a residence time of 24 hours. About 50%-60% of lignin in the substrate are solubilized in the caustic extraction and 40%-50% of condensed lignin remain. The product slurry exiting the caustic extraction tower is gravity fed into a single stage vacuum rotary vacuum washer where hot water or filtrate at a ratio 5:1 to the solid is used to wash the soluble lignin from the solids.

The mixture is chemically treated with 4-stage sodium chlorite/acetic acid anhydrous to remove lignin and extractives. Total charges in these stages are 10% (based on sodium chlorite), which is about 1.1 times the lignin content of the mixture. 40% of chemical charge is applied in the first stage, and the remaining 60% is divided equally among the three subsequent stages. The ratio of sodium chlorite to acetic acid anhydrous (by weight) is kept the same, 5 to 1, in all stages.

The temperature of the reactor is maintained in the range of 120-180 Fahrenheit; and the residence time of the reactor is 2 hours. After exiting from the first stage reactor, the solid is separated from the filtrate without washing. The solid is sent to the subsequent stages, where fresh solution of sodium chlorite, acetic acid anhydrous is added at the beginning of each stage. Process conditions such as temperature, pressure, and residence time in the subsequent stage are identical to the first stage.

The product slurry exiting the last sodium chlorite/acetic acid tower is gravity fed into a single stage vacuum rotary vacuum washer where hot water or filtrate from the chlorination filtrate at a ratio 5:1 to the solid is used to wash the remaining caustic/lignin from the solids.

Approximately 2% total chlorine, of which 70% is elemental chlorine (chlorine liquid can be used) and 30% is chlorine dioxide (about 0.6%) on weight of solids, are added and mixed to the washed solids. Steam is added to raise the temperature to about 40 Centigrade. The pH should be controlled to 2-3 by adding either acid or caustic to the mixture. Water or preferably filtrate from the chlorine washer is added to get a solids content of 3-4% by weight. The residence time of this stage is approximately 30 to 60 minutes.

After chlorination/chlorine dioxide stage, the solids again is washed with fresh hot water. Wash water usage is typically controlled to a dilution factor of 3, at exit consistency of 12%. Excess chlorination washer filtrate containing chlorinated lignin, phenols, extractives, after satisfying the dilution and process dilution uses, are mixed with filtrate from the caustic extraction stage washer. The combined filtrates can be evaporated to high solids concentration, 50-70% solids, and can be used to convert to chemicals, fuels or incinerated for steam and power. Cellulose degradation in the caustic and chlorination extraction/delignification stages are minimal, typically from 1% to 3% yield loss. The remaining solid is pure cellulose, free of lignin, wood extractives, and hemicelluloses.

Ethanol fermentation can be carried out in two separate stages, for hemicellulose sugars and cellulose as described in example 1.

I claim:

1. A process of treating and fractionating a lignocellulosic feedstock into high-purity fermentable sugars and lignin to produce ethanol, wherein the feedstock is selected from the group consisting of a softwood and a hardwood, the process comprising:
   (a) obtaining logs and separating said logs into hardwood and softwood logs;
   (b) chipping the separated logs of step (a) into wood chips having a length or width of approximately ¼ inch to 1 inch and a thickness of ¼ inch;

(c) pre-hydrolyzing, said pre-hydrolyzing comprising:
  (i) charging into a pre-soak tank:
    (a') the wood chips obtained from step (b), wherein said wood chips have their natural moisture content; and
    (b') saw dust, fines, and over-size chips resulting from the chipping of step (b); and
  (ii) acid pre-soaking by contacting said charged wood chips of step (a') and said over-sized wood chips, saw dust, and fines of step (b') with an acid selected from the group consisting of sulfuric acid, nitric acid, and hydrochloric acid; wherein said acid is present in an amount of up to 5% acid by weight of the dry-weight of the charged wood chips obtained from step (a'); wherein said acid provides a pH in said pre-soak tank of between pH 2 and 3; and wherein said contacting comprises contacting for a time of up to 5 hours;
(d) centrifuging and draining the acid-presoaked wood chips obtained from step (c) to consistency of approximately 30% solids;
(e) preheating the centrifuged-and-drained material obtained from step (d) in a series of steam mixers;
(f) screw-feeding the preheated material into a pressurized reactor, wherein the reactor is pressurized to a reactor pressure of 150 psi to 1000 psi and heated to a reactor temperature of 150° C. to 300° C. by injecting into the reactor direct live steam and a gas selected from the group consisting of nitrogen, carbon dioxide, oxygen, and air; and then maintaining the screw-fed material in the pressurized reactor at said temperature and said pressure for a period of time of 1 minute to 30 minutes;
(g) blowing the steam-pressure-treated material obtained from step (f) into a series of blow tanks or flash tanks, thereby disintegrating the material into lignocellulosic solids comprising impregnable fibers and fiber bundles, wherein steam is recovered from the blow tanks and recycled into the steam mixers of step (e);
(h) pressing the lignocellulosic solids containing the impregnable fibers and fiber bundles thereby separating a pre-hydrolysate liquor from the solids, wherein said pressing further comprises recovering from the impregnable fibers and fiber bundles of said solids trapped hemicellulosic xylose, arabinose, galactose, mannose, and glucose by washing the solids in a series of counter-current washers;
(i) neutralizing the pre-hydrolysate liquor and a filtrate obtained from the counter-current washers obtained from step (h) by treating the liquor and the filtrate with lime at a pH of 8 to 10, at a temperature of 40° C. to 80° C., and for a period of time of about 30 minutes to about 180 minutes, thereby precipitating compounds which are toxic to fermentation, the precipitated compounds selected from the group consisting of furfural, a phenol-containing compound, and acetic acid;
(j) delignifying and deresinating the washed solids obtained from step (h) wherein said washed solids further comprise lignin, cellulose, and extractives, said delignifying and deresinating comprising either:
  (ia) charging the washed solids from step (h) into a four-stage, continuous, co-current delignification and deresination reactor; and mixing with a stock mixer in each stage in the four-stage reactor, the charged solids with a 1% to 10% solution based on the weight of the charged washed solids,
    (a') wherein the solution comprises (i') a delignifying oxidant selected from the group consisting of sodium chlorite, sodium hypochlorite, acidic hydrogen peroxide, a solution of chlorine-and-chlorine dioxide, and a combination thereof, and (ii') an acid selected from the group consisting of anhydrous acetic acid, acetic acid, peracetic acid, and sulfuric acid and wherein the ratio in said solution of said oxidant to said acid is from 3:1 to 6:1;
    (b') wherein each reactor stage comprises a residence time period between 3 hours and 4 hours and a reactor temperature between 120° F. and 180° F.;
    (c') wherein the four-stage total amount of delignifying oxidant relative to the amount of lignin and extractives in the solids of step (h), is an amount having a oxidant-to-lignin ratio of between 1:1 and 1.5:1;
    (d') wherein the total solution is distributed to each stage of the four-stage reactor the distributing consisting of distributing 40% to the first stage, 30% to the second stage, 20% to the third stage, and 10% to the fourth stage; and
  (ib) obtaining from the four-stage reactor solids and liquids exiting from each stage of the reactor and then washing the obtained solids and liquids by vacuum filtering the obtained solids and liquids, thereby producing a purified cellulose solid product and wherein said vacuum filtering further comprises combining the filtered liquid into a filtrate tank, thereby obtaining a lignin-containing liquid filtrate for lignin recovery;
  or:
  (ii) extracting the washed solids from step (h) with caustic at a temperature between 80° F. and 150° F. and for a period of time between 1 and 3 hours, then washing the caustic-extracted solids by vacuum filtering;
(k) further delignifying and purifying the purified cellulose solid material obtained from step (j)(ib) or the extracted-and-washed solid obtained from step (j)(ii) by mixing therewith a solution selected from the group consisting of chlorine-and-chlorine dioxide having a chlorine dioxide amount of 30% to 50% of the total chlorine in the solution or sodium chlorite-and-anhydrous acetic acid, wherein when a chlorine-and-chlorine dioxide solution or the sodium chlorite-and-anhydrous acetic acid solution is mixed at 120° F. and for a period of time of 3 hours, thereby providing a solids consistency of 3% to 10% solids and producing a cellulose solid product;
(l) washing the cellulose solid product of step (k) in a three-stage counter-current washer train to produce a purified cellulose solid product and a lignin-containing liquid filtrate;
(m) evaporating the lignin-containing liquid filtrate obtained from step (j)(ib) or step (l) by multiple-effect evaporators to 50% to 70% solids content, thereby recovering said lignin;
(n) enzymatically saccharifying or acid-hydrolyzing the purified cellulosic solids of step (l), thereby converting the purified cellulosic solids into a fermentable glucose; and
(o) fermenting the glucose obtained from step (n) and the xylose and arabinose from step (h) with a yeast or a bacterium, thereby producing said ethanol.

2. The process of claim 1, wherein:
the concentration of acid having up to 5% acid by weight in step (c)(ii) is in the range of 0.1% to 8% by volume;

wherein the recovered steam in step (g) is a saturated steam and is directly added to the steam mixers of step (e) and to the pressurized reactor of step (f);

wherein in step (j)(ia)(a') a combination of the oxidants and the acids are added to selectively delignify the solids obtained from step (h);

wherein in step (k) the solution is a chlorine-and-chlorine dioxide solution which is added to improve biological conversion and production of the ethanol; and wherein in step (m) the recovering lignin further comprises recovering the lignin as a lignin-containing liquor for incinerating in steam and power generation or for forming lignin-containing chemicals selected from the group consisting of drilling fluid aids and hydrocarbons feedstocks.

* * * * *